US00PP19460P2

(12) United States Plant Patent
White

(10) Patent No.: US PP19,460 P2
(45) Date of Patent: Nov. 18, 2008

(54) MINIATURE ROSE PLANT NAMED 'SAVATHOUGHTS'

(50) Latin Name: *Rosa hybrida*
Varietal Denomination: SAVathoughts

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/985,592

(22) Filed: Nov. 16, 2007

(51) Int. Cl.
*A01H 5/00* (2006.01)

(52) U.S. Cl. ..... Plt./118

(58) Field of Classification Search ..... Plt./118
See application file for complete search history.

*Primary Examiner*—Annette H Para
*Assistant Examiner*—S. B. McCormick-Ewoldt

(57) ABSTRACT

'SAVathougths' is a new and distinct variety of miniature rose plant, primarily identified by it's semi-double, bright orange flowers with orange-red edges and accents when grown in full sunlight. Flowers gradually fade to a complimentary yellow with lighter red accents, giving the appearance of orange and yellow flowers, all edged with red, on the plant at the same time. This plant will grow and bloom satisfactorily both in the greenhouse and outdoors, in the ground or in containers, providing bright decoration. Disease resistance has been shown to be outstanding for this rose in both California and Massachusetts.

1 Drawing Sheet

CROSS REFERENCE

This new invention may be compared to 'SAVaworry' (U.S. Plant. Pat. No. 17,787) from this same breeding program. The plant habit of 'SAVaworry' and this new invention is low and somewhat spreading, becoming wider than tall, and with pinnately compound leaves having 5 to 7 leaflets. Both cultivars may, at times, have just 12 petals. The flowers of both cultivars, when full open, are yellow and have red along the outer margins of the petals that is enhanced by the sun.

The lineage of these plants can be traced back to 'Little Darling' (U.S. Plant Pat. No. 1,581) which is found in the third generation for 'SAVaworry' and the fourth generation for this new invention; and to Rise 'n' Shine (U.S. Plant Pat. No. 4,231) in the fourth generation of the new invention and 'MORsherri' U.S. Plant Pat. No. 3,826) in the third generation of this new invention, both of which are in the third generation of 'SAVaworry'.

The differences between these two cultivars may first be seen in the flower. The flowers of 'SAVaworry' are a straw- to lemon-yellow and only the borders of the outer margins of the petals becoming an orange-red in the sun. The flowers of this new invention are a yellow-orange with red borders and accents on the petals in the sun. The foliage on this new invention is primarily 5-leaflet leaves with 7-leaflet leaves while the foliage on 'SAVaworry' is primarily 7-leaflet leaves with some 5-leaflet leaves.

Genus and species: *Rosa hybrida.*

Varietal denomination: 'SAVathoughts'.

BACKGROUND OF THE INVENTION

This present invention relates to a new and distinct variety of hardy, bush type plant of the miniature rose class. This variety was created by myself, Wendy R. White, under controlled conditions in a greenhouse in Rowley, Mass., by crossing the following two rose plants:

The seed parent is an unnamed, unpatented and unintroduced miniature seedling with orange-red flowers which was created from this same breeding program by crossing 'ROzorina' (U.S. Plant Pat. No. 2,321) by 'Baby Katie' U.S. Plant Pat. No. 4,471).

The pollen parent is an unnamed, unpatented and unintroduced miniature seedling with pale apricot-pink flowers, also from this same breeding program, created by crossing 'LAVjune' (U.S. Plant Pat. No. 6,859) by 'MACgenev' (U.S. Plant Pat. No. 8,279).

The idyllic goals of this breeding program were to create unique miniature roses with the qualities of exhibition, hybrid tea form blooms born in abundance from late spring to late fall on vigorous, well-branched and compact plants, with hardiness, disease resistance and fragrance. For this particular cross, the cultivar chosen as seed parent was known for its above average production of hybrid tea form blooms with moderate fragrance born on a vigorous, well-branched and compact plant. The cultivar chosen as pollen parent was known for exhibition, hybrid tea form blooms with mild fragrance born a compact plant. Neither parent had been fully evaluated for disease resistance or hardiness. The resulting new cultivar shows a combination of traits passed down through both parents. Its primary color appears to be from 'LAVjune'. The color of its flushing in full sunlight appears to be from 'ROzorina'. The shape of the leaflets and the leaflet count per leaf seems to be from 'Baby Katie'. The plant height of the new cultivar is the same as its pollen parent, about 10-inches, however, its pollen parent is very upright, only becoming 10-inches wide and the new cultivar may be up to 20 inches wide. The new cultivar has fewer petals than either parent, and its flowers are of a different color than those of either parent.

Asexual reproduction by cuttings of this new cultivar in Rowley, Mass., and Arroyo Grande, Calif., shows that all distinguishing characteristics of this rose continually come true to form.

BRIEF SUMMARY OF THE INVENTION

The present invention relates to a new, distinct and low growing variety of hardy, bush type, miniature rose plant, which is primarily characterized by its semi-double, bright yellow-orange flowers, edged and accented with red when grown in full sun. Other characteristics distinguishing it from all other varieties of which I am aware are its low-growing, upright yet spreading plant habit and the strength of its canes, and its high resistance to diseases. The variety is further characterized by:

Flowers borne mostly singly

Dark green, semi-glossy foliage

Repeat blooming habit from late spring to late fall

A moderate number of thorns

Easy to propagate from soft wood cuttings

A plant that grows and blooms satisfactorily both in the greenhouse and outdoors, providing decoration in the garden or containers.

BRIEF DESCRIPTION OF THE DRAWING

The accompanying drawing is of images taken from plants grown in a greenhouse under plastic in Arroyo Grande, Calif.

The upper image shows stems, leaves and prickles of this new invention in November.

The lower image shows flowers, stems, foliage and forming hips from plants in September.

Colors are as nearly correct as is possible to make in a color illustration of the character.

BOTANICAL DESCRIPTION OF THE PLANT

The following observations, measurements, values and comparisons describe plants of the miniature rose class of *Rosa hybrida*, 'SAVathougths', at 8 to 12 months old, growing in 3½-inch plastic pots, in a growing medium of peat moss and coconut bark, growing outside in Essex County, Mass. and a 6-year old plant growing in the ground for four years in Esex County, Mass. No significant difference was found between plants grown in pots compared to the one in the ground. A detailed descripton is presented here in outline form. Color references are made using The Royal Horticultural Society Colour Chart except where common terms of color are used. Phenotypic expression varies with environmental, cultural and climatic conditions, as well as differences in conditions of light and soil.

Flowers:

*Blooming habit.*—Cyclic to fast repeat from late spring to late fall.

*Borne.*—Mostly solitary.

*Bud.*—I. Size: ⅝-inch long and 15/32-inch diameter just before the sepals divide. II. Form: ovate with a truncate base and an acute apex.

*Sepals.*—I. Color outer surface: near 144A and lighter, between 144A and 145A, at the basal area and up into the center; A. Plants grown in full sun in Massachusetts had sepals entirely flushed with near 176A, from the Greyed-Orange Group, with areas flushed deeper, between 166A and 178A, into the Greyed-Red Group, and those areas exposed to the sun the longest are flushed even deeper with a color between 178A and 183A. B. Plants grown in California under plastic had minimal flushing. II. Color inner surface: medium yellow-green, near 147B, and much lighter, near 145B at the base and up through the center where it blends in with the near 147B. III. Texture and appearance: A. The outer surface is smooth and semi-glossy, with matte extensions. B. The inner surface has a very fine pubescence along the margins, decreasing towards the center, and ciliated margins that appear white, near 157D. IV. Characteristics: A. All sepals: 1. long, narrow, lanceolate. 2. extending ¾-inch beyond the tip of the bud just before the sepals start to divide. 3. ciliated margins. B. The two outer-most sepals: 1. Are 1⅛ to 1½-inches long and ¼-inch wide. 2. have 1 or sometimes 2 narrow, fusiform foliar appendages and 1 or 2 short filiform appendages. 3. have lanceolate apices. C. The two inner-most sepals: 1. are 13/16 to 15/16-inches long and 9/32- to 10/32-inch wide. 2. have attenuate apices and no foliar appendages. D. The one sepal in-between the inner and outer has characteristics of both the inner and outer sepals: 1. 1⅜- to 15/16-inches long and 4/16- to 5/16-inch wide. 2. one margin has 1 narrow, fusiform foliar appendage and 1 or 2 short filiform appendages; one margin has no foliar appendages. 3. the apex is attenuate. E. Sepals roll back: ahead of the petals, to the peduncle, and crossing over the peduncle. F. Sepals are permanently attached to the receptacle and remain attached as the hip forms, dropping as the hip begins to ripen.

*Receptacle.*—I. Diameter: 5/16-inch. II. Height: 9/32-inch, varying from 8/32- to 11/32-inch. III. Color: near 144A, and in direct sun, flushed heavily on the sunward side with near 175A.

*Peduncle.*—I. Length: varies from 1 1/16- to 2-inches. II. Diameter: ⅛-inch immediately beneath the receptacle and tapering to 3/32-inch at its base. III. Aspect: straight. IV. Strength: very strong. V. Color: lighter yellow-green, near 145A, right beneath the receptacle where there is no sun exposure, and the rest may be heavily flushed with a grayed orange-red color between 175A and 178A. VI. Appearance: semi-glossy to glossy. VII. Texture: glands toward the base. VIII. Foliar appeandages at the base: A. There is a pair of foliar appendages at the base of the peduncle, at its juncture with the stem. B. Appendages may be in one of the following forms and may be paired with any other formed foliar appendage. 1. a small, simple leaf attached with paired stipules the entire length of its petiole and joined with the base of the leaf. 2. tri-lobed or bi-lobed leaves with paired stipules along the petiole extending just to the base of the leaf blade. 3. three-leaflet leaf with stipules extending nearly the full length of the petiole. 4. connate stipules.

Bloom:

*I. Form.*—A. Opens with a truncate upper profile and a deeply cupped lower profile. B. Full open it has a flattened convex upper profile and a convex lower profile. C. Edges roll under with reflex increasing until full blown when they are rolled back creating the appearance of a pointed apex.

*II. Size.*—A. At exhibition stage, 2-inches in diameter. B. Full open, 2½- to 2⅞-inches in diameter and about 1 to 1⅛-inch deep. C. Before petal drop the bloom may expand to 3½-inches across and a profile depth of 1½-inches.

*III. Petalage.*—12 to 20 petals; 4 to 8 petaloids.

*IV. Fragrance.*—In full open bloom, mild fragrance has been noted, including Lily of Valley fragrance and other fragrances.

*V. Lasting time of bloom.*—From the time the sepals first separate until petals fade is about 2 weeks; petals drop cleanly from the receptacle.

Petals:

*I. Substance.*—Of medium thickness, with very good substance.

*II. Arrangement.*—Over-lapping, imbricated.

*III. Size.*—1- to 1⅛-inches long and 15/16- to 1⅛-inches wide.

*IV. Texture.*—Both upper and lower surfaces are satiny.

*V. Appearance.*—Surfaces are glabrous, with veins showing. A. Veins on adaxial surfaces are raised from the base of the petal and gradually reclining to flat with the surface at the margins. B. Veins on abaxial surfaces are raised from near the outer margin and gradually reclining toward the base.

*VI. Shape.*—A. Oblanceolate outer petals; spatulate intermediate petals; narrow-spatulate inner petals. B. Apex: apiculate. 1. with a small notch on either side of the point, most prominent on the outer-most petals. 2. inner petals have no notches or indents surrounding the point. C. Base: 1. outer petals have an obtuse base. 2. inner petals have an ovate base.

*VII. Color.*—A. When sepals first divide, near 32A–B, and which remains as a streak on the reverse of the outer petals. B. During the first few days, only the two outer petals on plants grown outside in direct sun: 1. adaxial surface: from the Greyed-Orange Group, between 169A and 170A, with a medium red between 44C and 34A along the outer margin, and a darker red near the apex, near 44B. a. basal area is an Indian Yellow near 17B and where it blends with the Greyed-Orange the color appears between 24A and 25A. b. The point of attachment is a light yellow-green near 154D. 2. The abaxial surface: a red-orange between 32A and 34C with blotches between 34A and 44A and Currant Red streaks near 46A. C. During the first few days, the rest of the petals: 1. adaxial surface, near 25B, Nasturtium Orange, margins near 25A, Orpiment Orange, basal area, near 14A, a deep orange-yellow. 2. abaxial surface, near 26B, Spanish Orange, blending into base a. Basal area, near 15A–B, Buttercup Yellow. D. When half blown,: 1. adaxial surface of the two outer petals is near 21B–C, medium red, near 44B, at the apex and along the margin, near 23C where the 44B and 21B–C blend, and a basal area near 14B–C. 2. abaxial surface of five to nine of the outer petals is a Lemon Yellow near 13B and flushed with Poppy Red near 40D, and the basal area is between 13B and 15B. a. the two outermost petals have streaks and blotches of near 44C that blend into the near 40D. b. the color at the apex is between 41A and 44B, which continues along the entire margin of just the two outermost petals except where they become near 44B at the apex. 3. adaxial surface of the inner petals is a Lemon Yellow near 13A with outer edges very lightly flushed with near 44D and upper half of the petals very slightly tinted with near 25B, and a basal area is also near 13A. 4. abaxial surface of the inner petals is Buttercup Yellow, near 15B, flushed with near 25B, and a basal area also near 15B. E. When full blown 1. adaxial surface of the outer petals is between 11C and 12D, with some areas exposed to the sun are flushed lightly with between 38A and 39C, and the basal area is near 13C. a. upper half of petals in three outer rows and the apex of all except the innermost petals is flushed heavily with near 47D, Geranium Lake. 2. abaxial surface of the outer petals is flushed near 37D, Shell Pink, with streaks of near 54A, the basal area is near 14C and the point of attachment is near 13C. a. abaxial surface of the two outermost petals also have streaks near 51D, Rhodonite Red. 3. adaxial surface of the inner petals is near 13C, flushed lightly with near 29C–D, near 47A at the apex, the basal area is near 13B–C and the point of attachment near 13B. 4. abaxial surface of the inner petals is flushed near 24D, near 47D at the apex, has a basal area near 13D, and point of attachment near 13C. F. As the bloom continues to age. 1. Colors from the flushing on the upper petal surfaces continue to deepen and intensify. 2. Colors of the reverse lighten slightly. G. General tonality. 1. Golden-yellow and orange bi-color. 2. From a distance, orange.

Petaloids:

*I. Width and length.*—A. Mostly three-fourths as long as the inner petals and ½- to ⅝-inch wide. B. Occasionally epipetalous and only ⅛-inch wide and ⅜- to ⅝-inch long.

*II. Unique characteristics.*—Somewhat deformed and narrower.

*III. Color.*—Same as the inner petals except a streak of the basal color up from the base to the apex.

Reproductive organs:

*Androecium.*—I. Stamens: quantity of 70 to 80, arranged regularly along the outer edge of the top of the receptacle. II. Anthers: color of an Indian Yellow near 17D. III. Pollen Sacs are a darker shade of Indian Yellow, near 17B. IV. Filaments: A. ⅛- to ¼-inch long. B. Color is near 23A, Cadmium Orange.

*Gynoecium.*—I. Pistils: quantity of 40 to 50, in the center of top surface of the receptacle. II. Styles: A. Straight, thin. B. Length of 3/32- to 4/32-inch. C. Color is a medium yellow, near 3D at the base and right below the stigma is a translucent medium pink near 53D. III. Stigmas: a medium yellow between 11B and 10C.

*Hips.*—I. Shape: Oblate. II. Size when mature: A. diameter varies from 23/32- to 30/32-inch. B. height varies from 19/32- to 25/32-inch, not respective to diameter. III. Surface: glabrous and glossy. IV. Color when mature: orange, near 28B and 28A and on the sunward side a red-orange, near 34A, deepening to near 44A on hips fully ripened in the sun. V. Seeds A. The color is usually a beige between 165D and 164C. B. Size of self-pollinated seeds is usually about 6/32- to 7/32-inch high by 4/32- to 5/32- inch by 3/32- to 4/32-inch wide.

*Plant.*—II. Habit is upright and well-branched, of miniature proportions in the rose class. III. Growth: A. Good vigor. B. Tested hardy zones 4 through 10. C. Top scoring rose nationally in 10 of 11 test gardens. D. Height is 10 to 12 inches, though it may put canes up to 16 to 18 inches. E. Width of plant may be up to 20 inches. F. Length of flowering stem measured to the base of the peduncle varies from 1¼ to 7¼ inches, depending on how low down on the plant it originates — blooms open just above the top of the plant canopy. G. Canes: 1. diameter: i. main canes is 5/16-inch. ii. primatery laterals is 3/16-inch. iii. flowering stems is 2/16-inch. 2. Color i. new growth is near 144A flushed on the sunward side with near 178D. ii. young growth— after a few weeks some canes become between 136C and 139C. iii. old wood — some canes may be near 146A–B and some between 136C and 139B, on the same plant. 3. Texture and appearance i. new wood: glabrous and semi-glossy. ii. old wood: glabrous and becoming matte. iii. lenticels were not noted on these plants. 4. Reproduction: initiates roots in 4 to 7 days from soft wood cuttings, under controlled greenhouse conditions; all distinguishing characteristics of this rose continually come true to form.

*Foliage*.—I. Pinnately compound with mostly 5, but also 7 and 3 leaflets. II. Quantity of leaves: 3 to 5 five- or seven-leaflet leaves per flowering stem, regardless the length of that stem. III. Size of mature leaf: 4 3/16-inches from stem to tip when measured along the rachis. IV. Leaflets: A. Ovate to broad-ovate with an acute apex and rounded base B. Mature terminal leaflet, 3/4- to 1 1/8-inches wide and 1 7/16- to 1 15/16-inches long. C. Substance: thick for this class. D. Upper surface — semi-glossy and glabrous, veins recessed slightly. E. Undersurface — matte and glabrous, main vein protrudes, primary lateral veins slightly raised. F. Edge — simple, near-even, fine serration; each serrature is tipped with a gland. G. color new foliage 1. upper surface is a medium green near 137A, with margins appearing near 187A, the color from the glands. 2. under surface is near 138A and flushed with near 183B–C, with veins of near 147C. 3. after a few weeks the upper surface becomes a darker green, near 139A; the reverse becomes near 191A, flushed with near 187A and veins appearing between 146D and 144C. H. Color old foliage 1. upper surface is between 139A and 149A and the main vein starts as near 145D, with no anthocyanin coloring on the leaflet-blades. 2. undersurface is between 138A and 137C and veins appear near 145A. 3. petioles, petiolules and the rachis are usually flushed with anthocyanin coloring on the mature leaves, with the possible exception of leaves near the base of the plant that might receive no direct exposure to the sun. IV. Petioles: A. Length on a five-leaflet leaf is 13/16-inch long with a diameter of 1/16-inch. B. Color on young leaf of the adaxial surface is near 145C in the groove and near 137A along the ridges. C. Color on mature leaf: 1. the adaxial surface is near 145C between the stipules and usually suffused lightly with near 187C–D. 2. above the stipules ridges are the color of the leaf blade and usually suffused heavily with near 187 B–C and the groove is near 145A and usually suffused lightly with near 187C. 3. color of the abaxial surface is near 144A–B between the stipules and above that point, near 146C. D. There are some hairs in the groove of the adaxial side and a few stipitate glands along the ridges; there are a few stipitate glands scattered on the abaxial side. V. Rachis A. Length on 5-leaflet leaf is 1 1/4-inch. B. Color on young leaf: the adaxial and abaxial surfaces is the same as the petiole. C. Color on mature leaf: the adaxial surface is usually heavily suffused with near 187A–B along the ridges and lightly suffused with near 187C in the groove; color of the abaxial surface is near 146C usually flushed very lightly with near 187A–B. D. There are a few hairs in the groove of the adaxial side and an occasional one along the ridges; there are more hairs and several stipes in the groove at the juncture with the petiolules; there may be an occasional stipe or soft prickle along the abaxial side and a few hairs at the junctures with the petiolules. VI. Petiolules A. Length to terminal leaflet on a five-leaflet leaf is 9/16-inch; B. Length to the other leaflets is 1/32-inch. C. Color of the petiolules to lateral leaflets is the same as that of the rachis; color to the terminal leaflet is near 146C and usually with flushing of near 187A–B just before it connects to the leaflet. D. The abaxial surface and the groove of the adaxial surface are usually glabrous; there may be glands or stipitate glands along the ridges of the adaxial surface near the juncture with the leaflet. VIII. Stipules A. On a mature leaf, usually 7/16- to 9/16-inch in length attached and 3/32-inch angled out at 50 to 55 degrees. B. Color on the adaxial surface of a mature leaf is near 145C and with the "flags" and along the margins of the upper half being between 139A and 141A and the center is usually flushed with near 187B–C. C. Color of the abaxial surface of a mature leaf is between 143C and 191A, usually with some flushing with near 187A-B. D. Stipitate glands give the appearance of the margins being finely dentate,; edges are tightly recurved.

*Prickles*.—I. Quantity: one to three per linear inch of stem. II. Length: varies from 6/32- to 9/32-inch. III. Shape: triangular with an acute tip. IV. Base: oval shaped; length is equal to the length of its prickle. V. Color: A. When young, near 145B and flushed near 184A on the sunward side. B. When old, medium brown, near 165B, and a very dark brown, near 165A, at the tip.

*Resistance*.—I. Excellent resistance to downey and powdery mildews, blackspot and rust. II. Very good resistance to aphids, whitefly, spider mites and thrip. Susceptible to rose midge.

What is claimed is:

1. A new and distinct variety of hardy miniature rose plant is claimed, with flowers of an orange blend, substantially as herein described and illustrated.

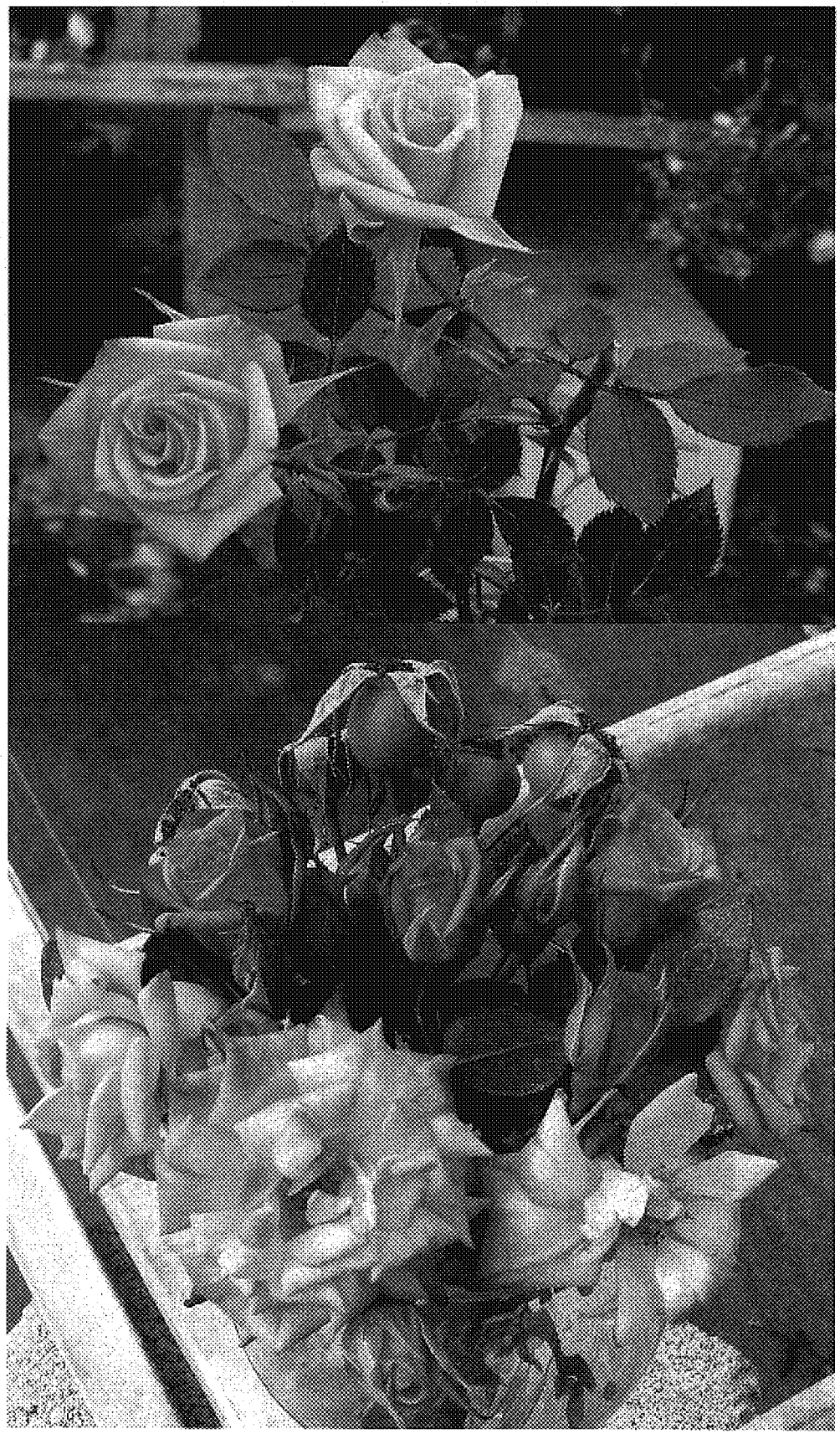

* * * * *